United States Patent [19]

Grollier et al.

[11] Patent Number: 4,602,913
[45] Date of Patent: Jul. 29, 1986

[54] USE OF HYDROXYANTHRAQUINONES FOR THE COLORATION OF HUMAN KERATIN FIBRES

[75] Inventors: Jean F. Grollier, Paris; Georges Rosenbaum, Asnieres; Jean Cotteret, Franconville, all of France

[73] Assignee: L'Oreal, Paris, France

[21] Appl. No.: 630,681

[22] Filed: Jul. 13, 1984

Related U.S. Application Data

[63] Continuation of Ser. No. 353,003, Feb. 26, 1982, abandoned.

[30] Foreign Application Priority Data

Feb. 27, 1981 [LU] Luxembourg .............................. 83177

[51] Int. Cl.$^4$ .............................................. A61K 7/13
[52] U.S. Cl. .......................................... 8/405; 8/406; 8/408
[58] Field of Search ........................... 8/405, 406, 408

[56] References Cited

U.S. PATENT DOCUMENTS

| | | | |
|---|---|---|---|
| 3,041,244 | 6/1962 | Feit et al. | 8/408 |
| 3,192,117 | 6/1965 | Kaiser et al. | 8/405 |
| 4,358,286 | 11/1982 | Grollier et al. | 8/405 |
| 4,425,132 | 1/1984 | Grollier et al. | 8/405 |

FOREIGN PATENT DOCUMENTS

| | | |
|---|---|---|
| 1379649 | 10/1964 | France . |
| 1391675 | 2/1965 | France . |
| 1401163 | 4/1965 | France . |
| 1422016 | 11/1965 | France . |
| 1430091 | 1/1966 | France . |
| 1574275 | 6/1969 | France . |
| 2106264 | 4/1972 | France . |

OTHER PUBLICATIONS

The Merck Index, 9th ed. 1976.
Chem. Abstracts 77:76672f Asymmetrically Substituted 1,3-dihydroxyanthraquinones, Lang, Mar. 9, 1972.
Chem. Abstracts 84:155510z Hair Tonic and Skin Cosmetic Preparations Containing Hydroxyanthraquinones, Ohtsu, Jan. 26, 1976.

Primary Examiner—Albert T. Meyers
Assistant Examiner—John M. Kilcoyne
Attorney, Agent, or Firm—Cushman, Darby & Cushman

[57] ABSTRACT

Use of hydroxyanthraquinones for the coloration of human keratin fibres, and process and composition in which they are used.

The composition contains, in a cosmetically acceptable medium, at least one hydroxyanthraquinone of the formula:

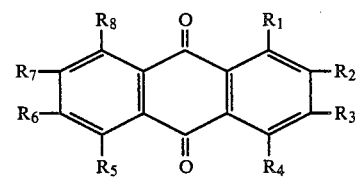

in which $R_1$, $R_2$, $R_3$, $R_4$, $R_5$, $R_6$, $R_7$ and $R_8$ independently of one another denote a hydrogen atom, a hydroxyl group, an alkyl group, an alkyl group substituted, for example, by a hydroxyl, amino or acyl group, an alkoxy group, a nitro group, a halogen group, a group $SO_3H$, $CHO$, $CO_2H$ or $SO_3Na$, or a group $-CO_2R'$, in which $R'$ denotes alkyl or an alkali metal, with the proviso that: at least two of the groups $R_1$, $R_2$, $R_3$, $R_4$, $R_5$, $R_6$, $R_7$ and $R_8$ denote hydroxyl, and that if $R_1$ and $R_2$ denote OH, $R_5$, $R_6$, $R_7$ and $R_8$ denoting hydrogen, then at least one of the two groups $R_3$ and $R_4$ is different from hydrogen, or alternatively if $R_1$ and $R_3$ denote OH, $R_2$ and $R_4$ denoting hydrogen and one or two of the substituents $R_5$, $R_6$, $R_7$ and $R_8$ denoting hydroxyl, then at least one of the substituents $R_5$, $R_6$, $R_7$ and $R_8$ is different from hydrogen, alkyl or halogen.

22 Claims, No Drawings

USE OF HYDROXYANTHRAQUINONES FOR THE COLORATION OF HUMAN KERATIN FIBRES

This is a continuation of application Ser. No. 353,003, filed Feb. 26, 1982, now abandoned.

The present invention relates to the use of hydroxyanthraquinones for the coloration of human keratin fibres, and in particular living hair, and to the coloration processes and the dyeing compositions in which these compounds are used.

Aminoanthraquinone derivatives have already been used for the direct coloration of the hair, see, for example, French Pat. Nos. 1,422,016, 1,391,675, 1,401,163, 1,379,649, 1,430,091 and 1,574,275. Furthermore, it has already been proposed to use certain hydroxyanthraquinones, described, in particular, in French Pat. No. 2,106,264 to colour the hair.

We have now discovered that, surprisingly, a particular class of hydroxyanthraquinones makes it possible to obtain coloration of human hair directly, even at ambient temperature. These compounds give rise to dyeings having a good resistance to light, washing, adverse weather conditions and perspiration. Furthermore, they make it possible to obtain a very wide variety of colorations.

These dyestuffs also have the advantage of being very stable in solution in the cosmetic media normally used for this type of dyeing.

Moreover, thse dyestuffs generally have a low toxicity as well as a good affinity, making them particularly suitable for dyeing of human hair.

This type of dyestuff had already been recommended for the dyeing of textile materials, in particular with mordanting agents such as derivatives of transition metals (chromium dyestuffs); these metals are unusable in the field of hair dyeing because of the risks of breakage to which they can give rise with subsequent treatments such as perming. The use of these compounds under the conditions of the dyeing of human hair has never been considered.

The hydroxyanthraquinones used according to the present invention for the coloration of human hair are more particularly characterised in that they correspond to the general formula:

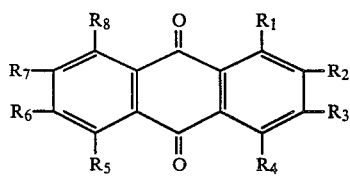

in which $R_1$, $R_2$, $R_3$, $R_4$, $R_5$, $R_6$, $R_7$ and $R_8$ independently of one another denote a hydrogen atom, a hydroxyl group, an alkyl group, an alkyl group substituted, for example, by a hydroxyl, amino or acyl group, an alkoxy group, a nitro group, a halogen group, an $SO_3H$, $CHO$, $CO_2H$ or $SO_3Na$ group or a $—CO_2R'$ group, in which $R'$ denotes alkyl or an alkali metal, with the proviso that: at least two of the groups $R_1$, $R_2$, $R_3$, $R_4$, $R_5$, $R_6$, $R_7$ and $R_8$ denote hydroxyl, and that if $R_1$ and $R_2$ denote OH, $R_5$, $R_6$, $R_7$ and $R_8$ denoting hydrogen, then at least one of the two groups $R_3$ and $R_4$ is different from hydrogen, or alternatively if $R_1$ and $R_3$ denote OH, $R_2$ and $R_4$ denoting hydrogen and one or two of the substituents $R_5$, $R_6$, $R_7$ and $R_8$ denoting hydroxyl, then at least one of the substituents $R_5$, $R_6$, $R_7$ and $R_8$ is different from hydrogen, alkyl or halogen.

The preferred alkyl groups have 1 to 4 carbon atoms and denote methyl or ethyl, in particular.

The alkali metals which $R'$ may represent are preferably sodium or potassium.

The compounds which are more particularly preferred according to the invention are the following compounds: 1,4-dihydroxyanthraquinone, 1,2,4-trihydroxyanthraquinone, 1,2,7-trihydroxyanthraquinone, 1,2,5,8-tetrahydroxyanthraquinone, 3-carboxy-1,2,4-trihydroxyanthraquinone, 2-carboxy-1-methyl-3,5,6,8-tetrahydroxyanthraquinone, 3-sulpho-1,2,4-trihydroxyanthraquinone, 3-sulpho-1,2-dihydroxyanthraquinone, 5,8-dichloro-1,4-dihydroxyanthraquinone and 1,8-dihydroxy-3-hydroxymethylanthraquinone.

Other compounds of particular value within the scope of the present invention are the following compounds: 1,2-dihydroxy-4-nitroanthraquinone, 2-sulpho-1,4-dihydroxyanthraquinone, 2,6-disulpho-1,4-dihydroxyanthraquinone, 3-nitro-1,2,4-trihydroxyanthraquinone, 1,2,5-trihydroxyanthraquinone, 3-sulpho-1,2,6-trihydroxyanthraquinone, 3-nitro-1,2,6-trihydroxyanthraquinone, 3-sulpho-1,2,7-trihydroxyanthraquinone, 3-sulpho-1,4,5-trihydroxyanthraquinone, 1,2,4,5,8-pentahydroxyanthraquinone, 1,2,4,5,6,8-hexahydroxyanthraquinone, 3,7-disulpho-1,2,4,5,6,8-hexahydroxyanthraquinone, 1,2,4,5,7,8-hexahydroxyanthraquinone, 3-nitro-1,2,4,5,7,8-hexahydroxyanthraquinone, 2-methyl-1,3-dihydroxyanthraquinone, 2-carboxy-1,3-dihydroxyanthraquinone, 2-methyl-1,6-dihydroxyanthraquinone, 6-methyl-1,2,5-trihydroxyanthraquinone, 5-carboxy-1,2,4-trihydroxyanthraquinone, 7-chloro-3-methyl-1,5,6,8-tetrahydroxyanthraquinone, 2-carboxy-3-methyl-1,5,6,8-tetrahydroxyanthraquinone, 3-methyl-1,2,4,7,8-pentahydroxyanthraquinone, 3-methyl-1,2,5,6,7,8-hexahydroxyanthraquinone, 3-methyl-6-methoxy-1,5,7,8-tetrahydroxyanthraquinone, 1,2,6-trihydroxyanthraquinone and 1,8-dihydroxy-3-carboxyanthraquinone.

The class of the hydroxyanthraquinones is particularly rich in natural compounds, these compounds being, in particular, polyhydroxyanthraquinones which are unsubstituted or substituted by carboxyl, halogen, alkyl or substituted alkyl groups.

Amongst the natural compounds belonging to the hydroxyanthraquinones defined above, the following may be mentioned more particularly:

TABLE 1

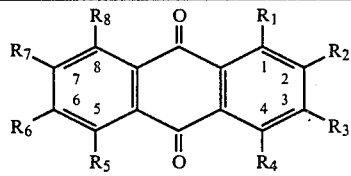

SUBSTITUENTS

| Common Name | $R_1$ | $R_2$ | $R_3$ | $R_4$ | $R_5$ | $R_6$ | $R_7$ | $R_8$ | Origin |
|---|---|---|---|---|---|---|---|---|---|
| 3-Methylalizarin | OH | OH | $CH_3$ | | | | | | Digitalis spp. |
| 6-Methylalizarin | OH | OH | | | | $CH_3$ | | | Hymenodycten excelsum - Coprosma parviflora |
| Xanthopurpurin | OH | | OH | | | | | | Rubia spp. - Gallium spp. etc. |
| Rubiadine | OH | $CH_3$ | OH | | | | | | Rubiatinctorium - Morinda spp. - Coprosma spp. |
| Lucidine | OH | $CH_2OH$ | OH | | | | | | Coprosma spp. - Asperula odorata |
| Nordamnacanthal | OH | CHO | OH | | | | | | Morinda spp. - Damnacanthus major |
| Munjistine | OH | COOH | OH | | | | | | Rubia spp. - Rubia cordifolia munjista |
| Chrysophanol | OH | | $CH_3$ | | | | | OH | Rheum spp. - Rumex - Rhamnus spp. |
| 2-Methylquinizarin | OH | $CH_3$ | | OH | | | | | Tectona granois |
| Soranjidiol | OH | $CH_3$ | | | | OH | | | Morinda spp. - Coprosma acerosa |
| Phomarin | OH | | $CH_3$ | | | OH | | | Phoma foveata - Digitalis spp. |
| Aloe emodin | OH | | $CH_2OH$ | | | | | OH | Aloe spp. - Asphodelus albus |
| Rhein | OH | | COOH | | | | | OH | Rheum spp. - Rumex spp. - Cassia spp. |
| Anthragallol (and methyl ethers) | OH | OH | OH | | | | | | Coprosma lucida - Rubia tinctorium |
| | OH | OH | $OCH_3$ | | | | | | |
| | $OCH_3$ | OH | OH | | | | | | |
| | OH | $OCH_3$ | OH | | | | | | |
| Purpurin | OH | OH | | OH | | | | | Rubia spp. - Gallium spp. - Asperula odorata |
| Pseudopurpurin | OH | OH | COOH | OH | | | | | Rubia spp. - Gallium spp. - Asperula spp. |
| Morindone | OH | $CH_3$ | | | OH | OH | | | Morinda spp. - Coprosma australis |
| Obtusifoline | $OCH_3$ | OH | $CH_3$ | | | | | OH | Cassia obtusifolia |
| Juzunol | $OCH_3$ | $CH_2OH$ | OH | | OH | | | | Damnacanthus major |
| Norjuzunal | OH | CHO | OH | | OH | | | | Damnacanthus major |
| Juzunal | $OCH_3$ | CHO | OH | | OH | | | | Damnacanthus spp. |
| Asperthecin | OH | OH | $CH_2OH$ | | OH | OH | | OH | Aspergillus spp. |
| Macrosporin | | $CH_3$ | OH | | | | $OCH_3$ | | Altenaria spp. |
| Coelulatin | OH | $CH_2OH$ | OH | | | | | OH | Coelospermun reticulatum |
| Physcion | OH | | $CH_3$ | | | $OCH_3$ | | OH | Rheum spp. - Rumex spp. |
| Questin | OH | | $CH_3$ | | | OH | | $OCH_3$ | Penicillium frequentans - Aspergillus terreus |
| Questinol | OH | | $CH_2OH$ | | | OH | | $OCH_3$ | Penicillium frequentans |
| 7-Chloroemodin (and methyl ethers) | OH | | $CH_3$ | | | OH | Cl | OH | Nephroma laevigatum- Caloplaca spp. |
| | OH | | $CH_3$ | | | $OCH_3$ | Cl | OH | |
| | $OCH_3$ | | $CH_3$ | | | OH | Cl | OH | |
| 5,7-Dichloroemodin | OH | | $CH_3$ | | Cl | OH | Cl | OH | Anaptychia obscurata |
| 7-Chlorocitrorosein | OH | | $CH_2OH$ | | | OH | Cl | OH | Aspergillus tumigatus |
| Fallacinol | OH | | $CH_2OH$ | | | $OCH_3$ | | OH | Teloschistes spp. - Xanthoria spp. |
| Carviolin | $OCH_3$ | | $CH_2OH$ | | | OH | | OH | Penicillium roseopupureum |
| Fallacinal | OH | | CHO | | | $OCH_3$ | | OH | Xanthoria spp. - Caloplaca spp. |
| Emodic acid | OH | | COOH | | | OH | | OH | Penicillium cyclopium - Xanthoria parietina |
| Parietinic acid | OH | | COOH | | | $OCH_3$ | | OH | Xanthoria spp. - |

TABLE 1-continued

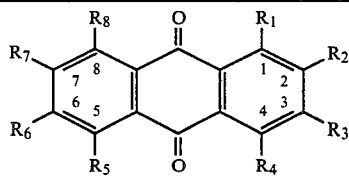

SUBSTITUENTS

| Common Name | $R_1$ | $R_2$ | $R_3$ | $R_4$ | $R_5$ | $R_6$ | $R_7$ | $R_8$ | Origin |
|---|---|---|---|---|---|---|---|---|---|
| Endocrocin | OH | $CO_2H$ | $CH_3$ | | | OH | | OH | Caloplaca spp. Nephromopsis endocrocea |
| Dermolutein | OH | COOH | $CH_3$ | | | OH | | $OCH_3$ | Dermocybe |
| 5-Chloro-dermolutein | OH | COOH | $CH_3$ | | Cl | OH | | $OCH_3$ | Dermocybe spp. |
| Dermocybin | OH | | $CH_3$ | | | OH | $OCH_3$ | OH | Cortinarius sanguneus |
| Nalgiovensin | OH | | $CH_2CHCH_3$ \| OH | | | $OCH_3$ | | OH | Penicillium nalgiovensis |
| Nalgiolaxin | OH | | $CH_2CHCH_3$ \| OH | | | $OCH_3$ | Cl | OH | Penicillium nalgiovensis |
| Ptilometric acid | OH | COOH | n-$C_3H_7$ | | | OH | | OH | Ptilometra australis |
| Islandicin | OH | | $CH_3$ | OH | | | | OH | Penicillium spp. |
| Helmintho-sporin | OH | | $CH_3$ | | OH | | | OH | Pyrenolora graminea - Helminthosporium spp. |
| Digitopurpon | OH | | $CH_3$ | OH | OH | | | | Digitalis purpura |
| Copareolatin (and methyl ethers) | | | $CH_3$ | OH | | OH | OH | OH | Coprosma areolata |
| 7-Hydroxy-emodin | OH | | $CH_3$ | | | OH | OH | OH | Heliococcus confusus |
| Dermoglaucin | OH | | $CH_3$ | | | $OCH_3$ | OH | OH | Cortinarius sanguineus |
| Majoronal | OH | CHO | OH | OH | $OCH_3$ | | | | Damnacanthus major |
| Isoerythro-laccin | OH | OH | OH | | | OH | | $CH_3$ | Laccifer lacca |
| Cereoalbolinic acid | OH | OH | OH | | | OH | COOH | $CH_3$ | Ceroplastes ulbolineatus |
| Kermesic acid | OH | | OH | OH | | OH | COOH | $CH_3$ | Kermococcus ilicis |
| Carminic acid | OH | Gluco-side | OH | OH | | OH | COOH | $CH_3$ | Dactylopius coccus |
| Laccaic acid D | OH | | OH | | | OH | COOH | $CH_3$ | Laccifer lacca |
| Xanthorin | OH | | $CH_3$ | | OH | $CH_3$ | | OH | Xanthoria elegans - Laurera purpurina |
| Valsarin I | OH | | $CH_3$ | | OH | OH | Cl | OH | Valsaria rubricosa - Lasallia papulosa |
| Valsarin II | OH | | $CH_3$ | OH | | OH | Cl | OH | Valsaria rubricosa - Lasallia papulosa |
| Clavorubin | OH | COOH | $CH_3$ | | OH | OH | | OH | Claviceps purpurea |
| (Nor)solorinic acid | $CO(CH_2)_4CH_3$ | $COC_5H_{11}$ | OH | | | OH | | OH | Solorina crocea - Aspergillus versicolor |
| 2,5,7-Tri-hydroxyemodin | OH | OH | $CH_3$ | | OH | OH | OH | OH | Mypcoblastus sanguinarius |
| Boletol | OH | OH | | OH | COOH | ←or→ | | COOH | Boletus spp. |
| Dermorubin | OH | COOH | $CH_3$ | OH | | OH | | $OCH_3$ | Dermocybe spp. |
| 5-Chlorodermo-rubin | OH | COOH | $CH_3$ | OH | Cl | OH | | $OCH_3$ | Dermocybe spp. |
| Erythroglaucin | OH | | $CH_3$ | OH | | $OCH_3$ | | OH | Aspergillus spp. - Xanthoria elegans |
| Cynodontin | OH | | $CH_3$ | OH | OH | | | OH | Helminthosporium spp. |
| | OH | $CH_3$ | | OH | OH | $CH_3$ | | OH | Curvularia spp. etc. |
| Aurantioobtusin | $OCH_3$ | OH | $CH_3$ | | | OH | $OCH_3$ | OH | Cassia obtusifolia |
| Obtusin | $OCH_3$ | OH | $CH_3$ | | | $OCH_3$ | $OCH_3$ | OH | Cassia obtusifolia |
| 6-Methyl ether of rubro-comatulin | OH | | OH | $CO(CH_2)_2CH_3$ | OH | $OCH_3$ | | OH | Comatula spp. |
| Ventimalin | OH | | $CH_3$ | OH | | | OH | OH | Ventilago viminalis |

TABLE 1-continued

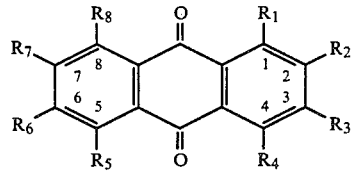

SUBSTITUENTS

| Common Name | R₁ | R₂ | R₃ | R₄ | R₅ | R₆ | R₇ | R₈ | Origin |
|---|---|---|---|---|---|---|---|---|---|
| Viminalin | OCH$_3$ | OH | CH$_3$ | OH | | | OH | OCH$_3$ | *Ventilago viminalis* |

The natural compounds can be used, within the scope of the present invention, either as such in the form of their isolated molecules or, if appropriate, in the form of C-glucosides or O-glucosides or in the form of extracts or plants in which they are present. The plants or plant extracts which are particularly preferred are those shown in Table 1 above.

The dyeing compositions for human hair, according to the present invention, are thus essentially characterised in that they contain at least one dyestuff corresponding to the formula (I) defined above, in a cosmetically acceptable medium.

The compositions preferably contain these dyestuffs in proportions of 0.005 to 10% by weight and preferably 0.01 to 7% by weight.

The compositions intended for dyeing human hair, according to the invention, can be presented in various forms such as liquids, creams, gels, oils, powders or any other form suitable for dyeing the hair. In particular, they can be packaged in aerosol flasks, in the presence of a propellent.

These compositions can be used in the form of colouring setting lotions, in which case application is not followed by rinsing, or in the form of colouring shampoos, dyes or colouring poultices, in which cases application is followed by rinsing and, if appropriate, by shampooing.

A particularly preferred embodiment of the compositions according to the invention is in the form of poultices. In this case, the hydroxyanthraquinones according to the invention, and preferably the hydroxyanthraquinones of natural origin, which can be in the different forms mentioned above, are prepared in the form of a powder which is stable on storage, and are introduced into a solid medium which can be a powder, flour or a starchy or mucilaginous substance, and which is diluted at the time of use with an appropriate liquid so as to form a mixture having an appropriate consistency for application to the hair.

The powders used in the poultices according to the invention can be insoluble substances such as silicas, plants, clays, plants pulverised after solvent extraction of their active principles, or plants containing the hydroxyanthraquinones of natural origin, according to the invention. The liquid used to dilute the powder can be water and/or a cosmetically acceptable solvent such as an alcohol, glycol or oil. The viscosity generally obtained after mixing is from 300 to 3,500 centipoises.

It is of course possible to introduce, in addition to the hydroxyanthraquinones of natural origin, other hydroxyanthraquinones according to the invention and also other natural or synthetic dyestuffs. Other natural dyestuffs which may be mentioned in this respect are lawsone, juglone, indigo, and the plants or extracts in which these dyestuffs are present.

The cosmetically acceptable medium of the other embodiments of dyeing compositions for human hair, according to the invention, is generally aqueous, suitably having a pH from 2 to 11; it can be adjusted to the desired value with the aid of alkalising agents such as ammonia, alkali metal carbonates, alkanolamines such as mono-, di or tri-ethanolamine, and alkylamines, or acidifying agents such as hydrochloric acid, sulphuric acid or citric acid.

These compositions can also contain anionic, cationic, non-ionic and/or amphoteric surface-active agents or mixtures thereof. Amongst the preferred surface-active agents, there may be mentioned, more particularly, soaps, alkylbenzenesulphonates, alkylnaphthalenesulphonates, sulphates, ether-sulphates and sulphonates of fatty alcohols, quanternary ammonium salts such as trimethylcetylammonium bromide and cetylpyridinium bromide, fatty acid diethanolamides, polyoxyethyleneated or polyglycerolated acids, alcohols or amides, and polyoxyethyleneated or polyglycerolated alkylphenols. The surface-active agents are typically present in the compositions according to the invention in proportions of 0.1 to 55% by weight and preferably 1 to 40% by weight, relative to the total weight of the composition.

The compositions can also contain organic solvents for solubilising compounds which would not otherwise be sufficiently soluble in water. Examples of these solvents include lower alkanols such as ethanol and isopropanol, polyols such as glycerol, glycol or glycol ethers, such as ethylene glycol monobutyl ether, ethylene glycol, propylene glycol, and diethylene glycol monoethyl ether and monomethyl ether, and analogous products or mixtures thereof. These solvents are preferably used in proportions from 1 to 60% by weight and more particularly from 3 to 30% by weight, relative to the total weight of the composition.

The compositions can also contain anionic, non-ionic, cationic or amphoteric polymers, suitably in proportions from 0.1 to 5% by weight.

The compositions according to the invention can be thickened, preferably with sodium alginate, gum arabic, cellulose derivatives such as methylcellulose, hydroxyethylcellulose, hydroxypropylmethylcellulose and carboxymethylcellulose, and various polymers serving this purpose, such as acrylic acid derivatives. It is also possible to use inorganic thickeners such as bentonite. These thickeners are preferably present in proportions of 0.1 to 5% by weight and in particular 0.5 to 3% by weight, relative to the total weight of the composition.

Reducing agents and antioxidants, such as sodium sulphite, thioglycolic acid, thiolactic acid, sodium bisulphite, ascorbic acid and hydroquinone, can also be included in the compositions according to the invention. These reducing agents and antioxidants are advantageously present in the composition in proportions of 0.05 to 1.5% by weight, relative to the total weight of the composition.

Of course, any other adjuvants normally used in hair-dyeing compositions, such as penetrating agents, sequestering agents, buffers and perfumes, can be included in the compositions according to the invention.

It is self-evident that the compositions according to the invention can also contain other direct dyestuffs, especially anthraquinone dyestuffs other than the hydroxyanthraquinones used in this invention, azo dyestuffs, nitrobenzene derivatives, indophenols, indamines and indoanilines, and hydroxyl derivatives of benzaldehyde.

The compositions according to the invention can also contain so-called oxidation dyestuffs, that is to say compounds which are not in themselves dyestuffs, but which are converted to dyestuffs by condensation in an oxidising medium. The oxidation dyestuffs are divided, on the one hand, into oxidation dyestuff precursors of the para type, generally diaminobenzenes, diaminopyridines and aminophenols, in which the functional groups are in the para-position relative to one another, and oxidation dyestuff precursors of the ortho type, in which the functional groups are in the ortho position relative to one another, and on the other hand, into compounds referred to as modifiers, toners or couplers, which are so-called meta derivatives, generally meta-diaminobenzenes, meta-diaminopyridines, meta-aminophenols, meta-diphenols and also phenols.

These compositions can also contain so-called "rapid" oxidation dyestuffs, which are dyestuff precursors of the benzene series which contain, on the nucleus, three substituents which are hydroxyl, methoxy or amino groups and which are capable of oxidising directly in air.

The dyestuffs are preferably present in proportions from 0.005 to 10% by weight.

Particularly advantageous results can be obtained for the compositions defined above containing polyhydroxyanthraquinones which are unsubstituted or substituted by non-acidic groups and which preferably have alkaline pH values from 7 to 12.

If the compositions according to the invention contain polyhydroxyanthraquinones substituted by acid groups such as carboxyl or sulphonic acid groups, particularly advantageous results are obtained for acid pH values of 2 to 7.

The hair-dyeing process according to the invention is essentially characterised in that at least one composition of this invention is applied to the hair, before or after shampooing, and left on the hair for, say, 5 to 60 minutes and preferably 5 to 40 minutes, and the hair is rinsed and dried. A composition in the form of a setting lotion can also be applied to the hair, after shampooing, and the hair is then dried.

The coloration of the hair can also be carried out according to processes comprising several steps, at least one of which consist in applying a dyestuff of the formula (I). These multi-step processes can use compositions having different pH values according to the nature of the dyestuffs present. Within the scope of the invention, it is possible, in particular, to envisage multi-step dyeing using first a composition containing polyhydroxyanthraquinones with acidic groups and having a pH of 2 to 7, and, in a second step, a composition containing a polyhydroxyanthraquinone having an alkaline pH of 7 to 12 or vice versa.

The following Examples further illustrate the present invention.

EXAMPLE 1

The following composition is prepared:

| | |
|---|---|
| 1,2,4-Trihydroxyanthraquinone | 1 g |
| Lanette wax O | 20 g |
| Copra monoethanolamide | 5 g |
| SIPON LA 30 | 10 g |
| 2-Amino-2-methylpropanol q.s.p. | pH 10 |
| Distilled water q.s.p. | 100 g |

This composition is a claret-coloured cream.

When applied to a natural chestnut head of hair for 30 minutes, it imparts to the hair, after rinsing, shampooing and drying, a very luminous mahogany-red sheen.

EXAMPLE 2

The following composition is prepared:

| | |
|---|---|
| 1,2,4,-Trihydroxy-3-carboxyanthraquinone | 0.05 g |
| Vinyl acetate/crotonic acid (90/10) copolymer | 1.8 g |
| Vinylpyrrolidone/vinyl acetate (60/40) copolymer | 0.4 g |
| 96° strength ethyl alcohol q.s.p. | 50° alcoholic strength |
| Triethanolamine q.s.p | pH 6 |
| Distilled water q.s.p | 100 g |

This purple setting lotion is applied to a deep blond head of hair. After shaping and drying, the hair is embellished with an iridiscent sheen.

EXAMPLE 3

The following composition is prepared:

| | |
|---|---|
| Sodium salt of 1,2-dihydroxy-3-sulphoanthraquinone monohydrate | 1.0 g |
| Lawsone | 0.3 g |
| Cetyl alcohol | 17.0 g |
| MERGITAL CS 15/E | 6.0 g |
| Oleyl alcohol | 3.0 g |
| Citric acid q.s. | pH 3 |
| Distilled water q.s.p. | 100 g |

This yellow-coloured cream is applied to light chestnut hair.

After an interval of 20 minutes, followed by rinsing, the head of pair possesses a deep coppery-red sheen.

EXAMPLE 4

The following composition is prepared:

| | |
|---|---|
| 1,2,5,8-Tetrahydroxyanthraquinone | 0.7 g |
| 1,4-Dihydroxyanthraquinone | 1.3 g |
| Lanette wax O | 20.0 g |
| Copra monoethanolamide | 5.0 g |
| SIPON LA 30 | 10.0 g |
| 2-Amino-2-methylpropanol q.s. | pH 9.6 |
| Distilled water q.s.p | 100 g |

This composition constitutes a purplish-blue/brown-coloured cream.

It is applied to a chestnut head of hair for 30 minutes.

After rinsing, shampooing and drying, the hair possesses an ashen sheen.

EXAMPLE 5

The following composition is prepared:

| | |
|---|---|
| 1-Methyl-2-carboxy-3,5,6,8-tetra-hydroxyanthraquinone | 0.6 g |
| 3-Carboxy-1,2,4-trihydroxyanthraquinone | 0.3 g |
| Cetyl alcohol | 17.0 g |
| MERGITAL CS 15/E | 6.0 g |
| Oleyl alcohol | 3.0 g |
| Citric acid q.s | pH 2.7 |
| Distilled water q.s.p | 100 g |

This carmine-coloured cream is applied to light chestnut hair for 30 minutes.

After rinsing, shampooing and drying, this hair is shaded with a purple-violet sheen.

EXAMPLE 6

The following composition is prepared:

| | |
|---|---|
| 1,2,5,8-Tetrahydroxyanthraquinone | 0.6 g |
| 1-N—(β-Hydroxyethyl)-amino-2-methoxy-4-nitrobenzene | 0.2 g |
| 1-N—(β-Hydroxyethyl)-amino-3-nitro-4-aminobenzene | 0.1 g |
| SACTIPON 8533 | 25.0 g |
| Coconut fatty acid diethanolamide | 5.0 g |
| 2-Butoxyethanol | 1.0 g |
| Monethanolamine q.s | pH 9.6 |
| Distilled water q.s.p | 100 g |

This foaming liquid, which has a deep violet-brown colour, is a colouring shampoo.

It is applied to a light chestnut head of hair containing a considerable percentage of white hair.

After an interval of 15 minutes, followed by rinsing, the hair is coloured in an ashen, light chestnut shade and the white hair is covered with the same tint.

EXAMPLE 7

The following composition is prepared:

| | |
|---|---|
| Sodium salt of 1,2-dihydroxy-3-sulpho-anthraquinone monohydrate | 0.1 g |
| Vinyl acetate/crotonic acid (90/10) copolymer | 1.8 g |
| Vinylpyrrolidone/vinyl acetate (60/40) copolymer | 0.4 g |
| 96° strength ethyl alcohol q.s.p | 50° alcoholic strength |
| Triethanolamine q.s. | pH 5 |
| Distilled water q.s.p. | 100 g |

This composition constitutes a setting lotion, which is applied to a blond head of hair.

After shaping and drying, the hair possesses a pearlescent golden sheen.

EXAMPLE 8

The following composition is prepared:

| | |
|---|---|
| 1,2,7-Trihydroxhanthraquinone | 0.4 g |
| 1-Amino-2-nitro-4-hydroxybenzene | 0.1 g |
| 1-N—(β-Hydroxyethyl)-amino-2-nitro-4-hydroxybenzene | 0.3 g |
| Lanette wax O | 20.0 g |
| Copra monoethanolamide | 5.0 g |
| SIPON LA 30 | 10.0 g |
| 2-Amino-2-methylpropanol q.s.p. | pH 9.9 |
| Distilled water q.s.p. | 100 g |

This red-brown cream is applied to deep chestnut hair.

After 30 minutes, the product is rinsed out.

After shampooing and drying, a head of hair dyed with an intense and deep coppery-red sheen is obtained.

EXAMPLE 9

The following composition is prepared:

| | |
|---|---|
| 1,2,4-Trihydroxyanthraquinone | 0.05 g |
| 1,2,5,8-Tetrahydroxyanthraquinone | 0.3 g |
| Para-toluylenediamine dihydrochloride | 0.5 g |
| Para-aminophenol | 0.1 g |
| Meta-aminophenol | 0.1 g |
| Resorcinol | 0.4 g |
| Hydroquinone | 0.15 g |
| SINNOPAL NP9 | 22.0 g |
| SINNOPAL NP4 | 22.0 g |
| Propylene glycol | 11.0 g |
| 96° strength ethyl alcohol | 8.0 g |
| 35° B strength sodium bisulphite solution | 1.3 g |
| Pentasodium salt of diethylenetriamine-pentaacetic acid | 2.4 g |
| 22° B strength ammonia solution | 10.2 g |
| Distilled water q.s.p. | 100 g |

On dilution with an equal weight of hydrogen peroxide of 20 volumes strength, this black-violet liquid composition gives a gel, which is applied to a deep blond head of hair for 30 minutes.

After rinsing and shampooing, the hair is coloured in an ashen, light blond shade.

EXAMPLE 10

The following composition is prepared:

| | |
|---|---|
| 1-Methyl-2-carboxy-3,5,6,8-tetrahydroxyanthraquinone | 5.0 g |
| Juglone | 1.0 g |
| Rye flour | 15.0 g |
| Pulverised frangula | 15 g |
| Pulverised horse-chestnut leaves | 60.0 g |
| Citric acid | 4.0 g |

This yellowish powder is mixed with 3.5 times its weight of warm water at the time of use. The mixture obtained, which has a pH of 3.3 and a brick-red colour, has the consistency of a poultice.

When applied to blond hair for 20 minutes, it imparts to the hair, after rinsing and shampooing, a luminous golden sheen.

EXAMPLE 11

| | |
|---|---|
| 5,8-Dichloro-1,4-dihydroxyanthraquinone | 0.7 g |
| Lanette wax O | 20 g |
| Copra monoethanolamide | 5 g |
| Sipon LA 30 | 10 g |
| 2-Amino-2-methylpropan-1-ol q.s.p. | pH = 9.5 |
| Distilled water q.s.p. | 100 g |

This composition is a red-coloured cream. When applied to light blond hair for 30 minutes, it imparts to the hair, after rinsing, shampooing and drying, a pearlescent sheen.

EXAMPLE 12

| | |
|---|---|
| 1,8-Dihydroxy-3-hydroxymethylanthraquinone | 2 g |
| Powdered saponaria | 30 g |
| Maize cobs | 50 g |
| Wheat flour | 8 g |
| Anhydrous sodium carbonate | 10 g |

This beige-coloured powder is mixed with three times its weight of warm water at the time of use; the mixture thus obtained, which has a green-brown colour and a pH of 9.8, has the consistency of a poultice.

When applied to blond hair for 30 minutes, it imparts to the hair, after rinsing and drying, a coppery-beige sheen.

The various tradenames used in the foregoing examples are explained in greater detail below:

Lanette wax O: 50/50 mixture of cetyl alcohol and stearyl alcohol, sold by HENKEL SIPON LA 30: 20% strength solution of ammonium lauryl-sulphate, sold by HENKEL MERGITAL CS15/E: Cetyl-stearyl alcohol containing 15 mols of ethylene oxide, sold by HENKEL SACTIPON 8533: Sodium salt of sulphated oxyethyleneated alkanol, sold by LEVER SINNOPAL NP4: Nonylphenol oxyethyleneated with 4 mols of ethylene oxide, sold by HENKEL.

SINNOPAL NP 9: Nonylphenol oxyethyleneated with 9 mols of ethylene oxide, sold by HENKEL.

We claim:

1. A composition for dyeing human hair comprising in an aqueous medium for application to said hair 0.005 to 10 percent by weight of said composition of a compound of the formula

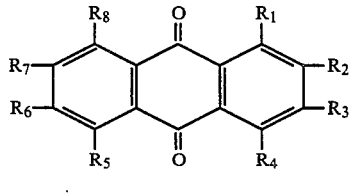

wherein $R_1$, $R_2$, $R_3$, $R_4$, $R_5$, $R_6$, $R_7$ and $R_8$ each independently represent hydrogen, hydroxyl, alkyl having 1–4 carbon atoms, alkyl having 1–4 carbon atoms and substituted by hydroxy, amino, acyl, halogen, $SO_3H$, CHO, $SO_3Na$ or —$CO_2R^1$ wherein $R^1$ represents alkyl having 1–4 carbon atoms or alkali metal, or said hydroxyanthraquinone is in the form of a glucoside, with the provisos that (i) at least two of $R_1$, $R_2$, $R_3$, $R_4$, $R_5$, $R_6$, $R_7$ and $R_8$ represent hydroxyl, (ii) if $R_1$ and $R_2$ represent OH, and $R_5$, $R_6$, $R_7$ and $R_8$ represent hydrogen, then at least one of $R_3$ and $R_4$ is other than hydrogen, and (ii) if $R_1$ and $R_3$ represent OH, $R_2$ and $R_4$ represent hydrogen and one or two of $R_5$, $R_6$, $R_7$ and $R_8$ represent hydroxyl, then at least one of $R_5$, $R_6$, $R_7$ and $R_8$ is other than said hydrogen, alkyl or halogen.

2. The composition of claim 1 which also contains a surface-active agent in an amount of 0.1 to 55 percent by weight relative to the total weight of said composition.

3. The composition of claim 1 which also includes a lower alkanol, glycerol or glycol ether, or a mixture thereof in an amount of 1 to 60 percent by weight relative to the total weight of said composition.

4. The composition of claim 1 which also includes, as a thickener, sodium alginate, gum arabic, methyl cellulose, hydroxyethyl cellulose, hydroxypropylmethyl cellulose or carboxymethyl cellulose, in an amount of 0.1 to 5 percent by weight relative to the total weight of said composition.

5. The composition of claim 1 which also includes, as a reducing agent and antioxidant, sodium sulphite, thioglycolic acid, thiolactic acid, sodium bisulphite, ascorbic acid or hydroquinone, in an amount of 0.05 to 1.5 percent by weight relative to the total weight of said composition.

6. The composition of claim 1 wherein $R_1$ to $R_8$ represent hydrogen, chlorine, hydroxyl, alkyl, hydroxyalkyl, $SO_3H$, $CO_2H$ or CHO.

7. The composition of claim 1 wherein said compound is selected from the group consisting of 1,4-dihydroxyanthraquinone, 1,2,4-trihydroxyanthraquinone, 1,2,7-trihydroxyanthraquinone, 1,2,5,8-tetrahydroxyanthraquinone, 3-carboxy-1,2,4-trihydroxyanthraquinone, 2-carboxy-1-methyl-3,5,6,8-tetrahydroxyanthraquinone, 3-sulpho-1,2-dihydroxyanthraquinone, 3-sulpho-1,2,4-trihydroxyanthraquinone, 5,8-dichloro-1,4-dihydroxyanthraquinone and 1,8-dihydroxy-3-hydroxymethylanthraquinone.

8. A composition according to claim 1 in which the hydroxyanthraquinone is selected from the group consisting of 2-sulpho-1,4-dihydroxyanthraquinone, 2,6-disulpho-1,4-dihydroxyanthraquinone, 1,2,5-trihydroxyanthraquinone, 3-sulpho-1,2,6-trihydroxyanthraquinone, 3-sulpho-1,2,7-trihydroxyanthraquinone, 3-sulpho-1,4,5-trihydroxyanthraquinone, 1,2,4,5,8-pentahydroxyanthraquinone, 1,2,4,5,6,8-hexahydroxyanthraquinone, 3,7-disulpho-1,2,4,5,6,8-hexahydroxyanthraquinone, 1,2,4,5,7,8-hexahydroxyanthraquinone, 2-methyl-1,3-dihydroxyanthraquinone, 2-carboxy-1,3-dihydroxyanthraquinone, 2-methyl-1,6-dihydroxyanthraquinone, 6-methyl-1,2,5-trihydroxyanthraquinone, 5-carboxy-1,2,4-trihydroxyanthraquinone, 7-chloro-3-methyl-1,5,6,8-tetrahydroxyanthraquinone, 2-carboxy-3-methyl-1,5,6,8-tetrahydroxyanthraquinone, 3-methyl-1,2,4,7,8-pentahydroxyanthraquinone, 1,2,6-trihydroxyanthraquinone, 1,8-dihydroxy-3-carboxyanthraquinone and 3-methyl-1,2,5,6,7,8-hexahydroxyanthraquinone.

9. The composition of claim 1 which has a pH from 7 to 12.

10. The composition of claim 1 which has a pH from 2 to 7.

11. A process for dyeing human hair comprises applying to said hair the composition of claim 1, permitting said composition to remain in contact with the hair for 5 to 60 minutes and then rinsing said hair.

12. The process of claim 11 which includes drying the rinsed hair.

13. A composition for dyeing human hair comprising in an aqueous medium for application to said hair 0.005 to 10 percent by weight of said composition of a compound of the formula

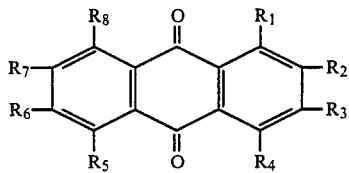

wherein
R$_1$, R$_2$, R$_3$, R$_4$, R$_5$, R$_6$, R$_7$ and R$_8$ each independently represent hydrogen, hydroxyl, alkyl having 1–4 carbon atoms, alkyl having 1–4 carbon atoms and substituted by hydroxy, amino, acyl, halogen, SO$_3$H, CHO, CO$_2$H, SO$_3$Na or —CO$_2$R$^1$ wherein R$^1$ represents alkyl having 1–4 carbon atoms or alkali metal, with the provisos that
(i) at least two of R$_1$, R$_2$, R$_3$, R$_4$, R$_5$, R$_6$, R$_7$ and R$_8$ represent hydroxyl,
(ii) if R$_1$ and R$_2$ represent OH, and R$_5$, R$_6$, R$_7$ and R$_8$ represent hydrogen, then at least one of R$_3$ and R$_4$ is other than hydrogen, and
(iii) if R$_1$ and R$_3$ represent OH, R$_2$ and R$_4$ represent hydrogen and one or two of R$_5$, R$_6$, R$_7$ and R$_8$ represent hydroxyl, then at least one of R$_5$, R$_6$, R$_7$ and R$_8$ is other than said hydrogen, alkyl or halogen.

14. The composition of claim 13 wherein said alkali metal is sodium or potassium.

15. A composition for dyeing human hair comprising in an aqueous medium for application to said hair 0.005 to 10 percent by weight of said composition of a compound of the formula

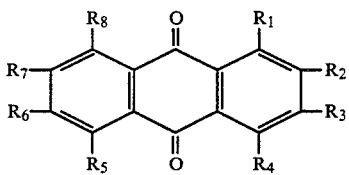

wherein the combinations of R$_1$ to R$_8$ are selected from the group consisting of
(1) R$_1$ and R$_2$ are each OH, R$_3$ is CH$_3$ and R$_4$, R$_5$, R$_6$, R$_7$ and R$_8$ are each hydrogen,
(2) R$_1$ and R$_2$ are each OH, R$_6$ is CH$_3$ and R$_3$, R$_4$, R$_5$, R$_7$ and R$_8$ are each hydrogen,
(3) R$_1$ and R$_3$ are each OH and R$_2$, R$_4$, R$_5$, R$_6$, R$_7$ and R$_8$ are each hydrogen,
(4) R$_1$ and R$_3$ are each OH, R$_2$ is CH$_3$ and R$_4$, R$_5$, R$_6$, R$_7$ and R$_8$ are each hydrogen,
(5) R$_1$ and R$_3$ are each OH, R$_2$ is CH$_2$OH and R$_4$, R$_5$, R$_6$, R$_7$ and R$_8$ are each hydrogen,
(6) R$_1$ and R$_3$ are each OH, R$_2$ is CHO and R$_4$, R$_5$, R$_6$, R$_7$ and R$_8$ are each hydrogen,
(7) R$_1$ and R$_3$ are each OH, R$_2$ is COOH and R$_4$, R$_5$, R$_6$, R$_7$ and R$_8$ are each hydrogen,
(8) R$_1$ and R$_8$ are each OH, R$_3$ is CH$_3$ and R$_2$, R$_4$, R$_5$, R$_6$ and R$_7$ are each hydrogen,
(9) R$_1$ and R$_4$ are each OH, R$_2$ is CH$_3$ and R$_3$, R$_5$, R$_6$, R$_7$ and R$_8$ are each hydrogen,
(10) R$_1$ and R$_6$ are each OH, R$_2$ is CH$_3$ and R$_3$, R$_4$, R$_5$, R$_7$ and R$_8$ are each hydrogen,
(11) R$_1$ and R$_6$ are each OH, R$_3$ is CH$_3$ and R$_2$, R$_4$, R$_5$, R$_7$ and R$_8$ are each hydrogen,
(12) R$_1$ and R$_8$ are each OH, R$_3$ is CH$_2$OH and R$_2$, R$_4$, R$_5$, R$_6$ and R$_7$ are each hydrogen,
(13) R$_1$ and R$_8$ are each OH, R$_3$ is COOH and R$_2$, R$_4$, R$_5$, R$_6$ and R$_7$ are each hydrogen,
(14) R$_1$, R$_2$ and R$_3$ are each OH and R$_4$, R$_5$, R$_6$, R$_7$ and R$_8$ are each hydrogen,
(15) R$_1$, R$_2$ and R$_4$ are each OH and R$_3$, R$_5$, R$_6$, R$_7$ and R$_8$ are each hydrogen,
(16) R$_1$, R$_2$ and R$_4$ are each OH, R$_3$ is COOH and R$_5$, R$_6$, R$_7$ and R$_8$ are each hydrogen,
(17) R$_1$, R$_5$ and R$_6$ are each OH, R$_2$ is CH$_3$ and R$_3$, R$_4$, R$_7$ and R$_8$ are each hydrogen,
(18) R$_1$, R$_3$ and R$_5$ are each OH, R$_2$ is CHO and R$_4$, R$_6$, R$_7$ and R$_8$ are each hydrogen,
(19) R$_1$, R$_2$, R$_5$, R$_6$ and R$_8$ are each OH, R$_3$ is CH$_2$OH and R$_4$ and R$_7$ are each hydrogen,
(20) R$_1$, R$_3$ and R$_8$ are each OH, R$_2$ is CH$_2$OH and R$_4$, R$_5$, R$_6$ and R$_7$ are each hydrogen,
(21) R$_1$, R$_6$ and R$_8$ are each OH, R$_3$ is CH$_3$, R$_7$ is Cl and R$_2$, R$_4$ and R$_5$ are each hydrogen,
(22) R$_1$, R$_6$ and R$_8$ are each OH, R$_3$ is CH$_3$, R$_5$ and R$_7$ are each Cl and R$_2$ and R$_4$ are each hydrogen,
(23) R$_1$, R$_6$ and R$_8$ are each OH, R$_3$ is CH$_2$OH, R$_7$ is Cl and R$_2$, R$_4$ and R$_5$ are each hydrogen,
(24) R$_1$, R$_6$ and R$_8$ are each OH, R$_3$ is COOH and R$_2$, R$_4$, R$_5$ and R$_7$ are each hydrogen,
(25) R$_1$, R$_6$ and R$_8$ are each OH, R$_2$ is COOH, R$_3$ is CH$_3$ and R$_4$, R$_5$ and R$_7$ are each hydrogen,
(26) R$_1$, R$_6$ and R$_8$ are each OH, R$_2$ is COOH, R$_3$ is n—C$_3$H$_7$ and R$_4$, R$_5$ and R$_7$ are each hydrogen,
(27) R$_1$, R$_4$ and R$_8$ are each OH, R$_3$ is CH$_3$ and R$_2$, R$_5$, R$_6$ and R$_7$ are each hydrogen,
(28) R$_1$, R$_5$ and R$_8$ are each OH, R$_3$ is CH$_3$ and R$_2$, R$_4$, R$_6$ and R$_7$ are each hydrogen,
(29) R$_1$, R$_4$ and R$_5$ are each OH, R$_3$ is CH$_3$ and R$_2$, R$_6$, R$_7$ and R$_8$ are each hydrogen,
(30) R$_4$, R$_6$, R$_7$ and R$_8$ are each OH, R$_3$ is CH$_3$ and R$_1$, R$_2$ and R$_5$ are each hydrogen,
(31) R$_1$, R$_6$, R$_7$ and R$_8$ are each OH, R$_3$ is CH$_3$ and R$_2$, R$_4$ and R$_5$ are each hydrogen,
(32) R$_1$, R$_2$, R$_3$ and R$_6$ are each OH, R$_8$ is CH$_3$ and R$_4$, R$_5$ and R$_7$ are each hydrogen,
(33) R$_1$, R$_2$, R$_3$ and R$_6$ are each OH, R$_7$ is COOH, R$_8$ is CH$_3$ and R$_4$ and R$_5$ are each hydrogen,
(34) R$_1$, R$_3$, R$_4$ and R$_6$ are each OH, R$_7$ is COOH, R$_8$ is CH$_3$ and R$_2$ and R$_5$ are each hydrogen,
(35) R$_1$, R$_3$, R$_4$ and R$_6$ are each OH, R$_2$ is glucoside, R$_7$ is COOH, R$_8$ is CH$_3$ and R$_5$ is hydrogen,
(36) R$_1$, R$_3$ and R$_6$ are OH, R$_7$ is COOH, R$_8$ is CH$_3$ and R$_2$, R$_4$ and R$_5$ are each hydrogen,
(37) R$_1$, R$_5$ and R$_8$ are each OH, R$_3$ and R$_6$ are each CH$_3$ and R$_2$, R$_4$ and R$_7$ are each hydrogen,
(38) R$_1$, R$_5$, R$_6$ and R$_8$ are each OH, R$_3$ is CH$_3$, R$_7$ is Cl and R$_2$ and R$_4$ are each hydrogen,
(39) R$_1$, R$_4$, R$_6$ and R$_8$ are each OH, R$_3$ is CH$_3$, R$_7$ is Cl and R$_2$ and R$_5$ are each hydrogen,
(40) R$_1$, R$_5$, R$_6$ and R$_8$ are each OH, R$_2$ is COOH, R$_3$ is CH$_3$ and R$_4$ and R$_7$ are each hydrogen,
(41) R$_3$, R$_6$ and R$_8$ are each OH, R$_1$ is CO(CH$_2$)$_4$CH$_3$, R$_2$ is COC$_5$H$_{11}$ and R$_4$, R$_5$ and R$_7$ are each hydrogen,
(42) R$_1$, R$_2$, R$_5$, R$_6$, R$_7$ and R$_8$ are each OH, R$_3$ is CH$_3$ and R$_4$ is hydrogen,
(43) R$_1$, R$_2$ and R$_4$ are OH, one of R$_5$ and R$_8$ is COOH and the other is hydrogen and R$_3$, R$_6$ and R$_7$ are each hydrogen,
(44) R$_1$, R$_4$, R$_5$ and R$_8$ are each OH, R$_3$ is CH$_3$ and R$_2$, R$_6$ and R$_7$ are each hydrogen,
(45) R$_1$, R$_4$, R$_5$, R$_8$ are each OH, R$_2$ and R$_6$ are each CH$_3$ and R$_3$ and R$_7$ are each hydrogen, and

(46) $R_1$, $R_2$, $R_4$, $R_7$ and $R_8$ are each OH, $R_3$ is $CH_3$ and $R_5$ and $R_6$ are each hydrogen.

16. A composition for dyeing human hair comprising in a solid carrier from 0.005 to 10 weight percent of a compound of the formula

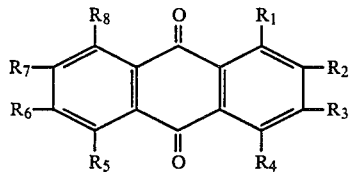

wherein the combinations of $R_1$ to $R_8$ are selected from the group consisting of (1) $R_1$ and $R_2$ are each OH, $R_3$ is $CH_3$ and $R_4$, $R_5$, $R_6$, $R_7$ and $R_8$ are each hydrogen,
(2) $R_1$ and $R_2$ are each OH, $R_6$ is $CH_3$ and $R_3$, $R_4$, $R_5$, $R_7$ and $R_8$ are each hydrogen,
(3) $R_1$ and $R_3$ are each OH and $R_2$, $R_4$, $R_5$, $R_6$, $R_7$ and $R_8$ are each hydrogen,
(4) $R_1$ and $R_3$ are each OH, $R_2$ is $CH_3$ and $R_4$, $R_5$, $R_6$, $R_7$ and $R_8$ are each hydrogen,
(5) $R_1$ and $R_3$ are each OH, $R_2$ is $CH_2OH$ and $R_4$, $R_5$, $R_6$, $R_7$ and $R_8$ are each hydrogen,
(6) $R_1$ and $R_3$ are each OH, $R_2$ is CHO and $R_4$, $R_5$, $R_6$, $R_7$ and $R_8$ are each hydrogen,
(7) $R_1$ and $R_3$ are each OH, $R_2$ is COOH and $R_4$, $R_5$, $R_6$, $R_7$ and $R_8$ are each hydrogen,
(8) $R_1$ and $R_8$ are each OH, $R_3$ is $CH_3$ and $R_2$, $R_4$, $R_5$, $R_6$ and $R_7$ are each hydrogen,
(9) $R_1$ and $R_4$ are each OH, $R_2$ is $CH_3$ and $R_3$, $R_5$, $R_6$, $R_7$ and $R_8$ are each hydrogen,
(10) $R_1$ and $R_6$ are each OH, $R_2$ is $CH_3$ and $R_3$, $R_4$, $R_5$, $R_7$ and $R_8$ are each hydrogen,
(11) $R_1$ and $R_6$ are each OH, $R_3$ is $CH_3$ and $R_2$, $R_4$, $R_5$, $R_7$ and $R_8$ are each hydrogen,
(12) $R_1$ and $R_8$ are each OH, $R_3$ is $CH_2OH$ and $R_2$, $R_4$, $R_5$, $R_6$ and $R_7$ are each hydrogen,
(13) $R_1$ and $R_8$ are each OH, $R_3$ is COOH and $R_2$, $R_4$, $R_5$, $R_6$ and $R_7$ are each hydrogen,
(14) $R_1$, $R_2$ and $R_3$ are each OH and $R_4$, $R_5$, $R_6$, $R_7$ and $R_8$ are each hydrogen,
(15) $R_1$, $R_2$ and $R_4$ are each OH and $R_3$, $R_5$, $R_6$, $R_7$ and $R_8$ are each hydrogen,
(16) $R_1$, $R_2$ and $R_4$ are each OH, $R_3$ is COOH and $R_5$, $R_6$, $R_7$ and $R_8$ are each hydrogen,
(17) $R_1$, $R_5$ and $R_6$ are each OH, $R_2$ is $CH_3$ and $R_3$, $R_4$, $R_7$ and $R_8$ are each hydrogen,
(18) $R_1$, $R_3$ and $R_5$ are each OH, $R_2$ is CHO and $R_4$, $R_6$, $R_7$ and $R_8$ are each hydrogen,
(19) $R_1$, $R_2$, $R_5$, $R_6$ and $R_8$ are each OH, $R_3$ is $CH_2OH$ and $R_4$ and $R_7$ are each hydrogen,
(20) $R_1$, $R_3$ and $R_8$ are each OH, $R_2$ is $CH_2OH$ and $R_4$, $R_5$, $R_6$ and $R_7$ are each hydrogen,
(21) $R_1$, $R_6$ and $R_8$ are each OH, $R_3$ is $CH_3$, $R_7$ is Cl and $R_2$, $R_4$ and $R_5$ are each hydrogen,
(22) $R_1$, $R_6$ and $R_8$ are each OH, $R_3$ is $CH_3$, $R_5$ and $R_7$ are each Cl and $R_2$ and $R_4$ are each hydrogen,
(23) $R_1$, $R_6$ and $R_8$ are each OH, $R_3$ is $CH_2OH$, $R_7$ is Cl and $R_2$, $R_4$ and $R_5$ are each hydrogen,
(24) $R_1$, $R_6$ and $R_8$ are each OH, $R_3$ is COOH and $R_2$, $R_4$, $R_5$ and $R_7$ are each hydrogen,
(25) $R_1$, $R_6$ and $R_8$ are each OH, $R_2$ is COOH, $R_3$ is $CH_3$ and $R_4$, $R_5$ and $R_7$ are each hydrogen,
(26) $R_1$, $R_6$ and $R_8$ are each OH, $R_2$ is COOH, $R_3$ is n—$C_3H_7$ and $R_4$, $R_5$ and $R_7$ are each hydrogen,
(27) $R_1$, $R_4$ and $R_8$ are each OH, $R_3$ is $CH_3$ and $R_2$, $R_5$, $R_6$ and $R_7$ are each hydrogen,
(28) $R_1$, $R_5$ and $R_8$ are each OH, $R_3$ is $CH_3$ and $R_2$, $R_4$, $R_6$ and $R_7$ are each hydrogen,
(29) $R_1$, $R_4$ and $R_5$ are each OH, $R_3$ is $CH_3$ and $R_2$, $R_6$, $R_7$ and $R_8$ are each hydrogen,
(30) $R_4$, $R_6$, $R_7$ and $R_8$ are each OH, $R_3$ is $CH_3$ and $R_1$, $R_2$ and $R_5$ are each hydrogen,
(31) $R_1$, $R_6$, $R_7$ and $R_8$ are each OH, $R_3$ is $CH_3$ and $R_2$, $R_4$ and $R_5$ are each hydrogen,
(32) $R_1$, $R_2$, $R_3$ and $R_6$ are each OH, $R_8$ is $CH_3$ and $R_4$, $R_5$ and $R_7$ are each hydrogen,
(33) $R_1$, $R_2$, $R_3$ and $R_6$ are each OH, $R_7$ is COOH, $R_8$ is $CH_3$ and $R_4$ and $R_5$ are each hydrogen,
(34) $R_1$, $R_3$, $R_4$ and $R_6$ are each OH, $R_7$ is COOH, $R_8$ is $CH_3$ and $R_2$ and $R_5$ are each hydrogen,
(35) $R_1$, $R_3$, $R_4$ and $R_6$ are each OH, $R_2$ is glucoside, $R_7$ is COOH, $R_8$ is $CH_3$ and $R_5$ is hydrogen,
(36) $R_1$, $R_3$ and $R_6$ are OH, $R_7$ is COOH, $R_8$ is $CH_3$ and $R_2$, $R_4$ and $R_5$ are each hydrogen,
(37) $R_1$, $R_5$ and $R_8$ are each OH, $R_3$ and $R_6$ are each $CH_3$ and $R_2$, $R_4$ and $R_7$ are each hydrogen,
(38) $R_1$, $R_5$, $R_6$ and $R_8$ are each OH, $R_3$ is $CH_3$, $R_7$ is Cl and $R_2$ and $R_4$ are each hydrogen,
(39) $R_1$, $R_4$, $R_6$ and $R_8$ are each OH, $R_3$ is $CH_3$, $R_7$ is Cl and $R_2$ and $R_5$ are each hydrogen,
(40) $R_1$, $R_5$, $R_6$ and $R_8$ are each OH, $R_2$ is COOH, $R_3$ is $CH_3$ and $R_4$ and $R_7$ are each hydrogen,
(41) $R_3$, $R_6$ and $R_8$ are each OH, $R_1$ is $CO(CH_2)_4CH_3$, $R_2$ is $COC_5H_{11}$ and $R_4$, $R_5$ and $R_7$ are each hydrogen,
(42) $R_1$, $R_2$, $R_5$, $R_6$, $R_7$ and $R_8$ are each OH, $R_3$ is $CH_3$ and $R_4$ is hydrogen,
(43) $R_1$, $R_2$ and $R_4$ are OH, one of $R_5$ and $R_8$ is COOH and the other is hydrogen and $R_3$, $R_6$ and $R_7$ are each hydrogen,
(44) $R_1$, $R_4$, $R_5$ and $R_8$ are each OH, $R_3$ is $CH_3$ and $R_2$, $R_6$ and $R_7$ are each hydrogen,
(45) $R_1$, $R_4$, $R_5$, $R_8$ are each OH, $R_2$ and $R_6$ are each $CH_3$ and $R_3$ and $R_7$ are each hydrogen, and
(46) $R_1$, $R_2$, $R_4$, $R_7$ and $R_8$ are each OH, $R_3$ is $CH_3$ and $R_5$ and $R_6$ are each hydrogen, said solid carrier being a powder, flour or a starch or mucilaginous substance.

17. The composition of claim 16 wherein said compound is 1-methoxy-2-carboxy-3,5,6,8-tetrahydroxyanthraquinone.

18. The composition of claim 16 wherein said compound is 1,8-dihydroxy-3-hydroxymethyl anthraquinone.

19. A process for dyeing human hair comprising admixing the composition of claim 16 with a liquid so that the resulting admixture has a viscosity from 300 to 3,500 centipoises, said liquid being water, an alcohol, glycol or oil, applying the resulting admixture to said hair and permitting said admixture to remain in contact with said hair for a period of time ranging from 5 to 60 minutes.

20. The process of claim 19 which includes rinsing the hair subsequent to contact of said composition with said hair for said period of time.

21. The process of claim 19 which includes washing the hair subsequent to contact of said composition for said period of time.

22. The process of claim 19 which includes rinsing and washing the hair subsequent to contact of said composition with said hair for said period of time.

* * * * *